(12) United States Patent
Tyler

(10) Patent No.: US 9,597,000 B2
(45) Date of Patent: *Mar. 21, 2017

(54) NERVE INTERFACE ELECTRODE WITH FIBERS FOR INSERTION BETWEEN NERVE FASCICLES

(71) Applicant: CASE WESTERN RESERVE UNIVERSITY, Cleveland, OH (US)

(72) Inventor: Dustin J. Tyler, Highland Heights, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/953,596

(22) Filed: Nov. 30, 2015

(65) Prior Publication Data

US 2016/0081569 A1   Mar. 24, 2016

Related U.S. Application Data

(63) Continuation of application No. 14/113,976, filed as application No. PCT/US2012/035027 on Apr. 25, 2012, now Pat. No. 9,254,378.

(60) Provisional application No. 61/478,664, filed on Apr. 25, 2011.

(51) Int. Cl.
  *A61B 5/04*   (2006.01)
  *A61N 1/05*   (2006.01)
  *A61B 5/00*   (2006.01)

(52) U.S. Cl.
  CPC .......... *A61B 5/04001* (2013.01); *A61B 5/686* (2013.01); *A61B 5/6877* (2013.01); *A61N 1/0529* (2013.01); *A61N 1/0551* (2013.01)

(58) Field of Classification Search
  CPC .......................... A61B 5/04001; A61N 1/0551
  USPC .......................................... 600/377; 607/116
  See application file for complete search history.

(56) References Cited

U.S. PATENT DOCUMENTS

| | | | |
|---|---|---|---|
| 8,639,311 B2 | 1/2014 | Giszter | |
| 9,254,378 B2 * | 2/2016 | Tyler | A61B 5/04001 |
| 2003/0176905 A1 | 9/2003 | Nicolelis et al. | |
| 2008/0228240 A1 | 9/2008 | Edell et al. | |
| 2009/0012593 A1 | 1/2009 | Benabid et al. | |
| 2009/0318590 A1 | 12/2009 | Weder et al. | |

FOREIGN PATENT DOCUMENTS

WO    2008091197 A1    7/2008

OTHER PUBLICATIONS

PCT International Search Report for PCT/US2012/035027 mailed Jul. 31, 2012, pp. 1-7.

(Continued)

*Primary Examiner* — Lee S Cohen
(74) *Attorney, Agent, or Firm* — Tarolli, Sundheim, Covell & Tummino LLP

(57) ABSTRACT

A nerve interface electrode has a plurality of conductive fibers. The fibers have a nonconductive sheath (108) surrounding a conducting wire. A conducting region (105) of the wire is exposed to the interior of the nerve (200). The fibers are configured for insertion between fascicles (204) of the nerve. In other teachings, a layer of polymer material configured to switch from a high strength/tensile modulus state to a low strength/tensile modulus state upon introduction of the fibers into the nerve is disposed on the fibers.

20 Claims, 8 Drawing Sheets

(56) References Cited

OTHER PUBLICATIONS

The Extended European Search Report for Application No. 15165137.9, mailed Sep. 15, 2015, pp. 1-7.

* cited by examiner

NERVE INTERFACE ELECTRODE WITH FIBERS FOR INSERTION BETWEEN NERVE FASCICLES

PRIORITY

This application is a continuation of U.S. application Ser. No. 14/113,976, filed Oct. 25, 2013, now U.S. Pat. No. 9,254,378, which is a U.S. National Stage application of PCT/US2012/035027, filed Apr. 25, 2012, which claims the benefit of U.S. Provisional Application No. 61/478,664, filed Apr. 25, 2011. The entire contents of these disclosures which is incorporated by reference as if fully set forth herein.

FIELD OF THE INVENTION

This disclosure is directed to nerve interfaces, such as peripheral nerve electrodes.

BACKGROUND

Nerve interfaces such as peripheral nerve electrodes allow recording and stimulation of nerve activity. For example, electrodes may be used to activate nerves connected to a particular muscle. One of the most important aspects of nerve interfaces is their ability to selectively activate or record nerve signals. For example, selective activation of single or small groups of fascicles can assist in "pure" activation of certain muscle groups, such as knee extensor muscles, with minimal activation of other non-synergistic muscle groups, for example hip flexors. In some instances, selective activation or recording of smaller groups or individual fascicles is desirable.

SUMMARY

In one embodiment, a nerve interface electrode comprising a plurality of conductive fibers is disclosed. The fibers comprise a nonconductive sheath surrounding a conducting wire. A conducting region of the wire is exposed to the interior of the nerve. The fibers are configured for insertion between fascicles of the nerve. In other embodiments, a layer of polymer material configured to switch from a high strength/tensile modulus state to a low strength/tensile modulus state upon introduction of the fibers into the nerve is disposed on the fibers. This configuration allows the fibers to be rigid prior to insertion but become flexible after insertion into the nerve.

In another embodiment of the present disclosure, a method of implanting a nerve interface electrode is disclosed. An electrode having multiple conductive fibers configured to flexibly disperse in a nerve in the region between the fascicles is selected. The fibers are inserted through the epineurium and into the nerve. The fibers then electrically stimulate the fascicles or record electrical activity within the nerve.

BRIEF DESCRIPTION OF THE DRAWINGS

It will be appreciated that the illustrated boundaries of elements in the drawings represent only one example of the boundaries. One of ordinary skill in the art will appreciate that a single element may be designed as multiple elements or that multiple elements may be designed as a single element. An element shown as an internal feature may be implemented as an external feature and vice versa.

Further, in the accompanying drawings and description that follow, like parts are indicated throughout the drawings and description with the same reference numerals. The figures may not be drawn to scale and the proportions of certain parts have been exaggerated for convenience of illustration.

DETAILED DESCRIPTION

Figure 1:
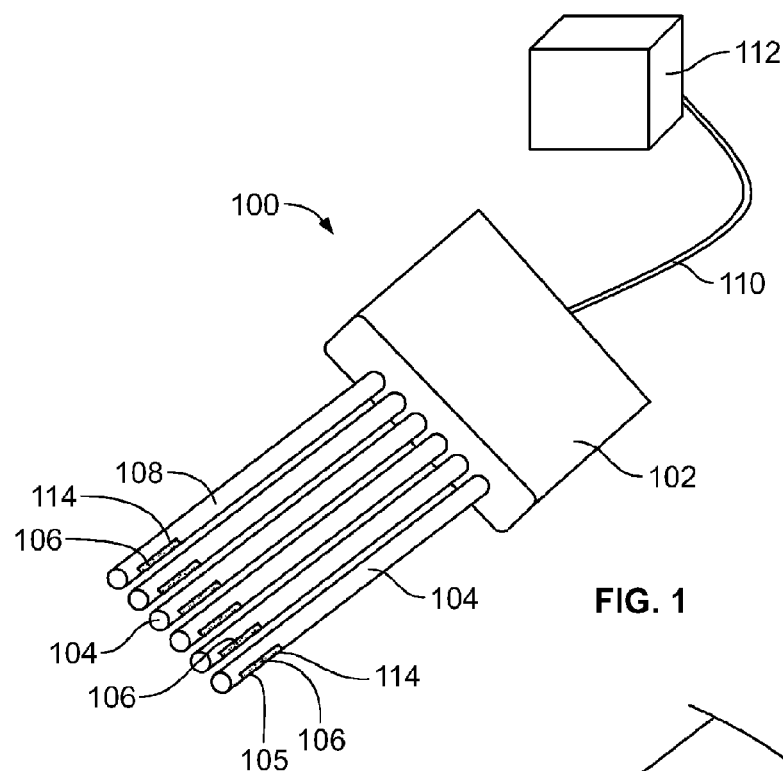
FIG. 1 illustrates an exemplary nerve interface 100.

Certain terminology will be used in the following description for convenience in describing the figures will not be limiting. The terms "upward," "downward," and other directional terms used herein will be understood to have their normal meanings and will refer to those directions as the drawing figures are normally viewed.

FIG. 1 illustrates a nerve interface 100 according to the present disclosure. The illustrated interface 100 has a housing 102 from which fibers 104 extend. In the illustrated embodiment, the fibers 104 have a nonconductive sheath 108 that covers a core of conductive wire 106 that is coupled to the control unit 112. Nonconductive sheath 108 covers a substantial portion of the surface of the wire 106, exposing only a portion of wire 106, corresponding to the conducting region 105, through sheath opening 114. The opening 114 may take a variety of shapes and sizes, but preferably exposes a conducting region 105 that faces a subset of the interior of the nerve 200, making the fiber 104 able, for example, to emit current in the direction the conducting region 105 faces while minimizing current emitted in other directions. As illustrated in FIG. 1, the sheath opening 114 exposes only a small portion of wire 106, allowing the fibers 104 to be directionally sensitive to received electrical signals and directionally selective in transmitting electrical signals. Throughout this disclosure, reference may be made to fibers 104 as stimulating nerves, while in other instances, fibers 104 may be described as recording nerve signals. It should be noted that, while the preferred embodiment stimulates and records electrically, the nerve interface need not be so limited according to the present disclosure. The fibers may be configured to detect, for example, different forms of energy transfer reflecting neuronal activity and communication, such as detection of the concentration particular chemicals. It should also be noted that the placement of the nerve interface 100 described in the present disclosure with regard to nerve stimulation will also be applicable in recording nerve signals.

Interface 100 is connected to control unit 112 by lead 110. Fibers 104 are each connected to the control unit 112, which may include monitoring circuitry, electrical signal generating circuitry, and a user interface. Several alternative implementations of control unit 112 and leads 110 are well known in the art and will not be discussed further herein. Fibers 104 have a longitudinal length much larger than the thickness of the generally cylindrical fibers 104 illustrated in the present disclosure. It should be noted that the fibers 104 illustrated in the current disclosure are not drawn to scale, and will preferably have a much thinner size relative to, for example, the nerve 200 shown in FIG. 2. Fibers 104 may have different cross-sectional shapes, such as elliptical, polygonal, or a combination of multiple shapes. In such cases, the length of fibers 104 will be much larger than a characteristic thickness of fibers 104 having such cross-sectional shapes.

Figure 2:
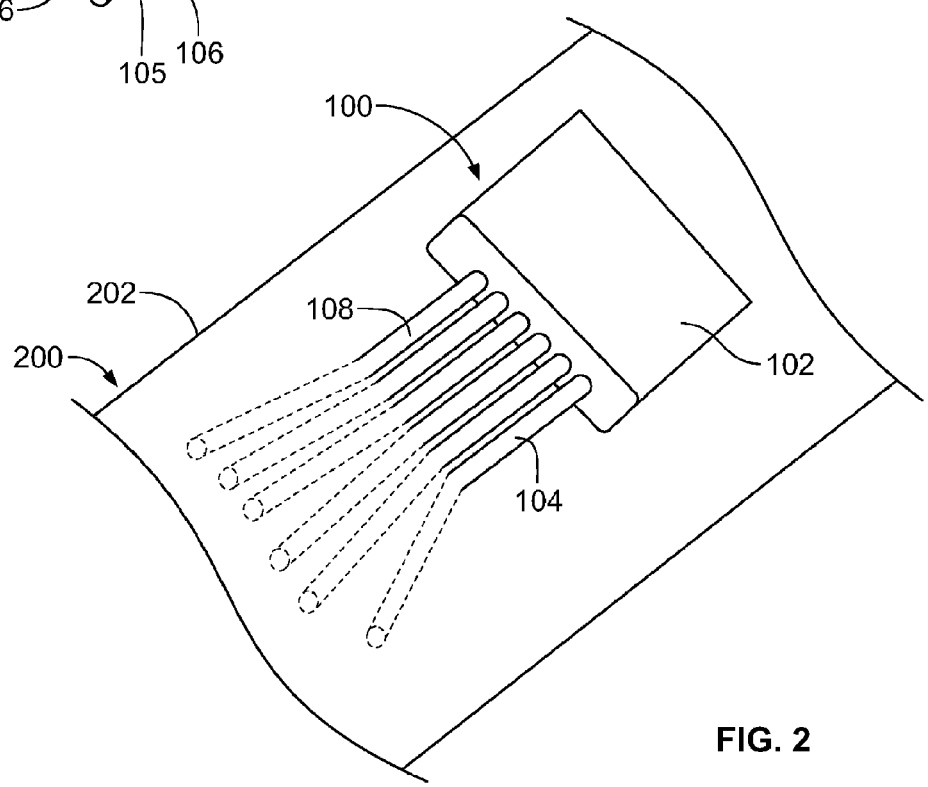
FIG. 2 illustrates a nerve interface 100 inserted through the epineurium 202 of nerve 200.

As shown in FIG. 2, the fibers 104 are inserted into the nerve 200 through the epineurium membrane 202. As will be discussed further below in connection with FIG. 3, insertion of the fibers 104 through the epineurium 202 exposes the portion of the fibers 104 that has penetrated the epineurium 202, which includes the conducting region 105 of the fibers 104, to the interior of the nerve 200. Fibers 104 may be used to pierce the epineurium 202. In such cases, the fibers 104 may be configured with sharp tips in order to more easily pierce the epineurium 202. The thinness of fibers 104 will aid in the insertion of the fibers 104 and minimize the disturbance to the nerve 200. Alternatively, separate incisions through which the fibers 104 are inserted may be made prior to insertion of fibers 104. Endoscopic and minimally invasive implantation are exemplary methods of implantation of fibers 104.

Figure 3:
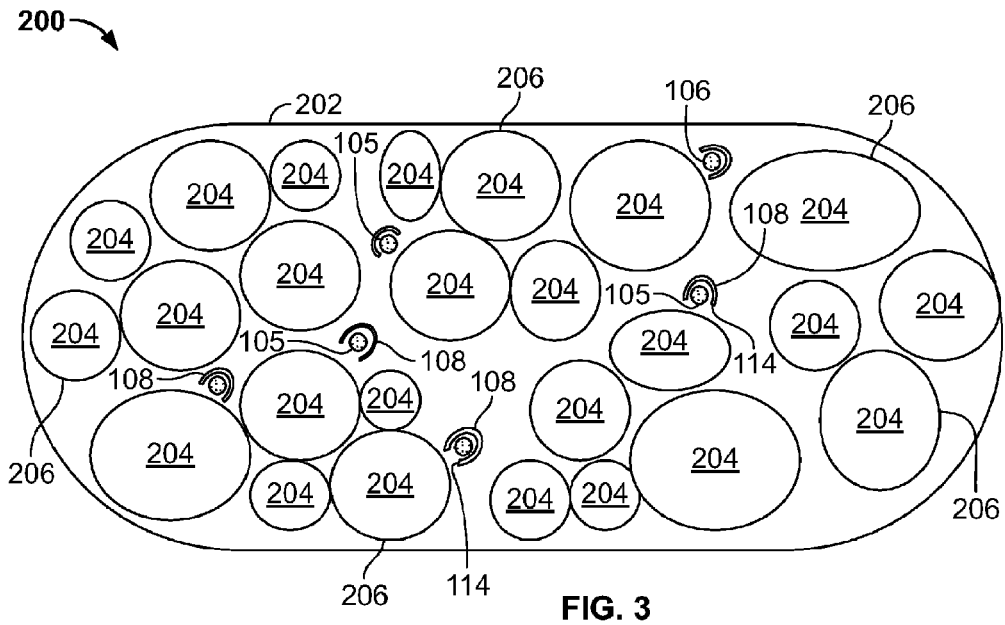
FIG. 3 illustrates a cross-sectional view along the nerve 200 after insertion of fibers 104.

FIG. 3 illustrates a cross-section of a peripheral nerve 200 after insertion of fibers 104. While a peripheral nerve 200 is used for purposes of illustration, the interface 100 according to the present invention will also be applicable to other types of nerve tissue, such as nerve tissue found in the central nervous system. The nerve 200 is surrounded by the epineurium membrane 202, or simply "epineurium." The nerve 200 contains several fascicles 204, which comprise bundles of axons. Each fascicle 204 is surrounded by a perineurium membrane 206, or simply "perineurium." FIG. 3 also illustrates the placement of fibers 104 throughout the interior of the nerve 200. Fibers 104 in the nerve 200 are flexible and so spread out, distributing themselves throughout the interior of the nerve 200 in the area between the fascicles 204. The fibers 104 do not penetrate the perineurium membrane 206, which minimizes trauma to the nerve 200. The distribution of fibers 104 between the fascicles 204 allows for improved selectivity in the control and measurement of individual fascicles 204 and their electrical activity.

As shown in FIG. 3, several conducting regions 105 of fibers 104 come into contact with perineurium membranes 206 of fascicles 204, while other conducting regions 105 are disposed adjacent but not in contact with a fascicles 206. In such an arrangement, fibers 104 can conduct electrical current in a directed manner, in the direction the conducting regions 105 face. This allows for relatively increased current density in the direction the conducting region 105 faces. This arrangement also allows for fibers 104 to be directionally sensitive when recording electrical activity. Fibers 104 will be most sensitive to electrical activity received from the direction the conducting region 105 faces. Further, in the illustrated configuration, fibers 104 may be placed nearby fascicles 204 located centrally within the nerve 200. Activation of an individual fiber 104 may stimulate a single fascicle 204 or multiple fascicles 204. This may in turn result in recruitment of additional fascicles 204 depending on the distribution of fascicles 204 in the nerve. Likewise, multiple fibers 104 may be activated, which may result in stimulation of multiple fascicles 204.

In addition to directed stimulation of individual fascicles 204, the fibers 204 may generate a desired electrical field ("field shaping") within the nerve 200 by selectively applying the appropriate level of electrical current to each of the fibers 104, the fibers 104 may create an electrical field that may selectively activate one or more fascicles 204, including fascicles 204 that are not adjacent to or in direct contact with a fiber 104.

In order to disperse among the spaces between the fascicles 204, the fibers 104 are preferably flexible. Flexibility allows the fibers 104 to disperse within the nerve 200, which allows for broader distribution of fibers 104, and therefore more selective control or recording of fascicles 204. However, flexibility can make insertion of the fibers 104 through the epineurium 202 more difficult. In one embodiment, the fiber 104 is coated with a layer of polymer nanocomposite material that has a variable tensile modulus and/or strength, switching from a high tensile modulus and strength to a low modulus and strength in response to introduction to the interior of the nerve 200. This layer may be part of the nonconductive sheath 108 or may be a separate layer. In the high tensile modulus/strength state, the polymer nanocomposite renders the fibers 104 rigid enough to puncture the epineurium 202. Such materials and the manner in which they may be manufactured are disclosed in U.S. Published Patent Application Nos. 2009/0318590 and 2008/0242765, incorporated herein by reference. For example, nanocomposite such as ethylene oxide-epichlorohydrin ("EO-EPI") combined with a cellulose matrix can exhibit high tensile strength in the absence of solvent. When an appropriate solvent, preferably a hydrogen-bond forming solvent, is introduced to the nanocomposite, the interactions giving the nanocomposite its strength are "switched off" by the competitive binding of the solvent. Other host polymers or copolymers may include, but are not limited to, various alkylene oxide polymers and copolymers such as ethylene oxide, propylene oxide, copolymers of ethylene oxide and epichlorohydrin and/or other monomers; a vinyl aromatic (co)polymer such as polystyrene and styrene copolymers; polyolefin polymers or copolymers such as polyethylene and polypropylene; diene polymers and copolymers, such as cis-polybutadiene; polyacrylates and acrylate copolymers, such as methyl methacrylate; polyamides; and polyester polymers or copolymers such as poly(vinyl acetate) or polycaprolactone.

Figure 4:
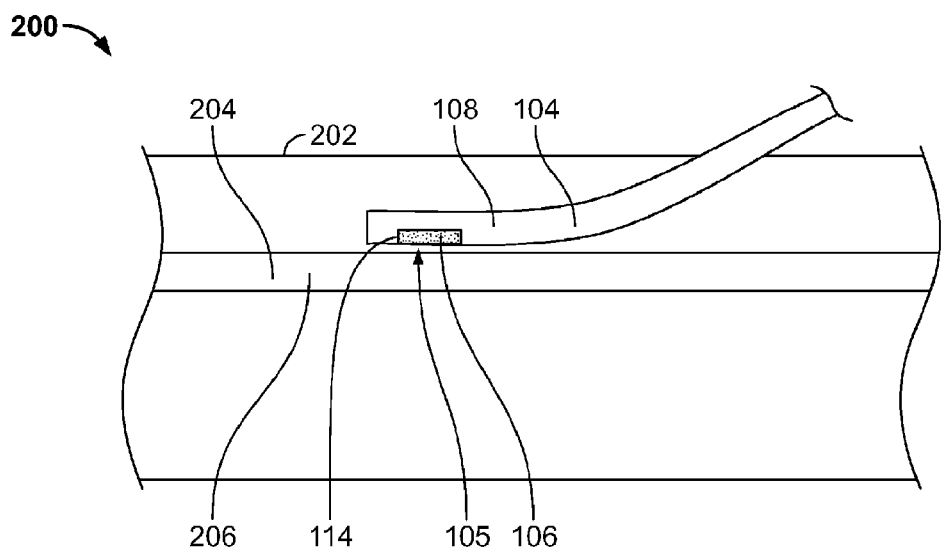
FIG. 4 illustrates a cross-sectional side view along the nerve 200 after insertion of fibers 104.

FIG. 4 illustrates a cross-sectional side view of a single fiber 104 inserted through the epineurium 202 and disposed adjacent a fascicle 204. In the illustrated embodiment, the fiber 104 is inserted through the epineurium 202 at an acute angle relative to the direction of the nerve 200. This configuration allows the fibers 104 to orient themselves parallel with the fascicles 204. As shown in FIG. 4, the conducting region 105 is disposed adjacent the perineurium membrane 206 of fascicle 204.

Figure 5:
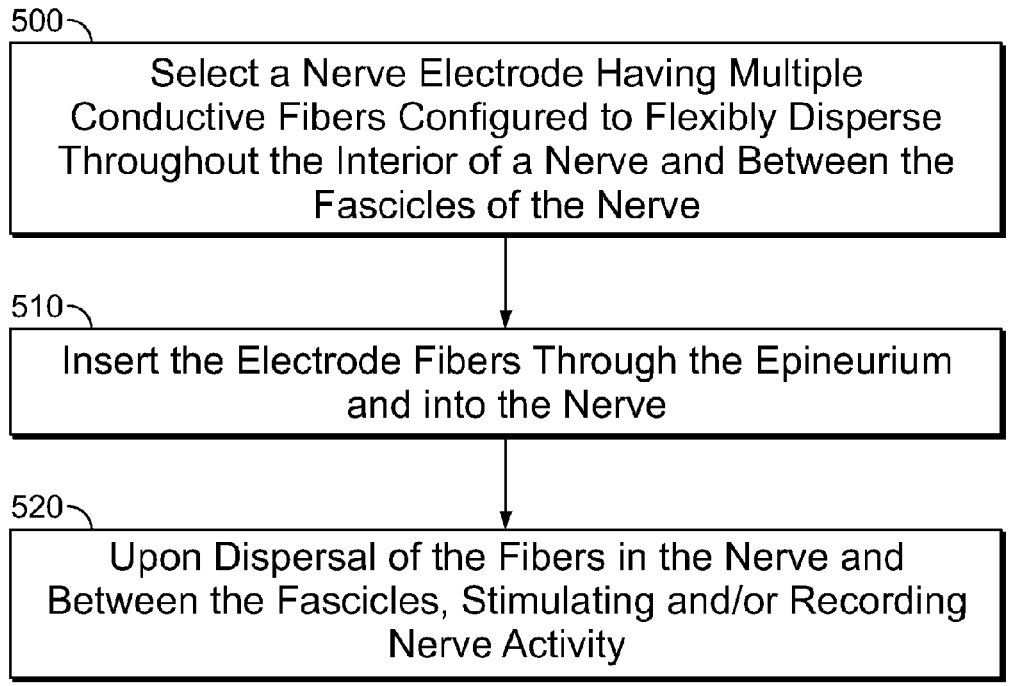
FIG. 5 illustrates exemplary method of implanting nerve interface 100.

As shown in FIG. 5, in one method of stimulation and/or recording of peripheral nerve electrical activity, an interface 100 having multiple conductive fibers 104 configured to flexibly disperse in the nerve 200 in the region between the fascicles 204 is selected in step 500. In another embodiment, an interface 100 having additional qualities such as fibers 104 each having a sheath 108 configured to switch from a high tensile modulus and strength to a relatively low tensile modulus and strength upon insertion into the nerve 200, thereby permitting the fibers 104 to flexibly disperse in the region in the nerve 200 between the fascicles 204, is selected. In yet another alternative embodiment, an interface 100 configured for insertion into a peripheral nerve is selected. In the illustrated embodiment, the electrode is then inserted through the epineurium 202 and into the nerve in step 510. Step 510 may be accomplished by a variety of approaches, such as an open surgical procedure, or alternatively a minimally invasive approach. In step 520, upon dispersal of the fibers 104 in the nerve 200 and between the fascicles 204, the fibers 104 record and/or stimulate nerve 200 activity.

Figure 6:
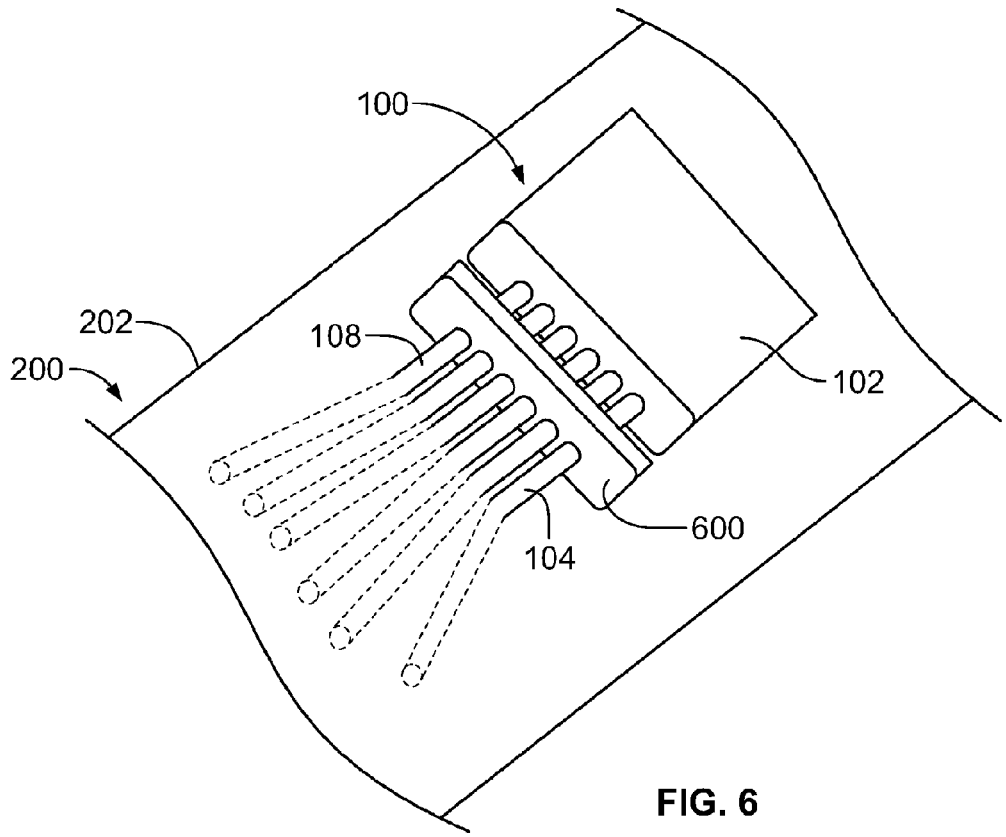
FIG. 6 illustrates a nerve interface 100 inserted through the epineurium 202 of nerve 200 with the aid of guide 600.

FIG. 6 illustrates an alternative embodiment of nerve interface 100 having a guide 600 that assists in insertion of fibers 104. The guide provides additional rigidity to the fibers 104 as they are inserted, for example when using the fibers 104 to penetrate the epineurium 202. The guide 600 reduces the length of fibers 104 that must kept rigid for insertion into nerve 200. The guide 600 may be placed adjacent the epineurium membrane 202 prior to insertion of fibers 104.

Figure 7:
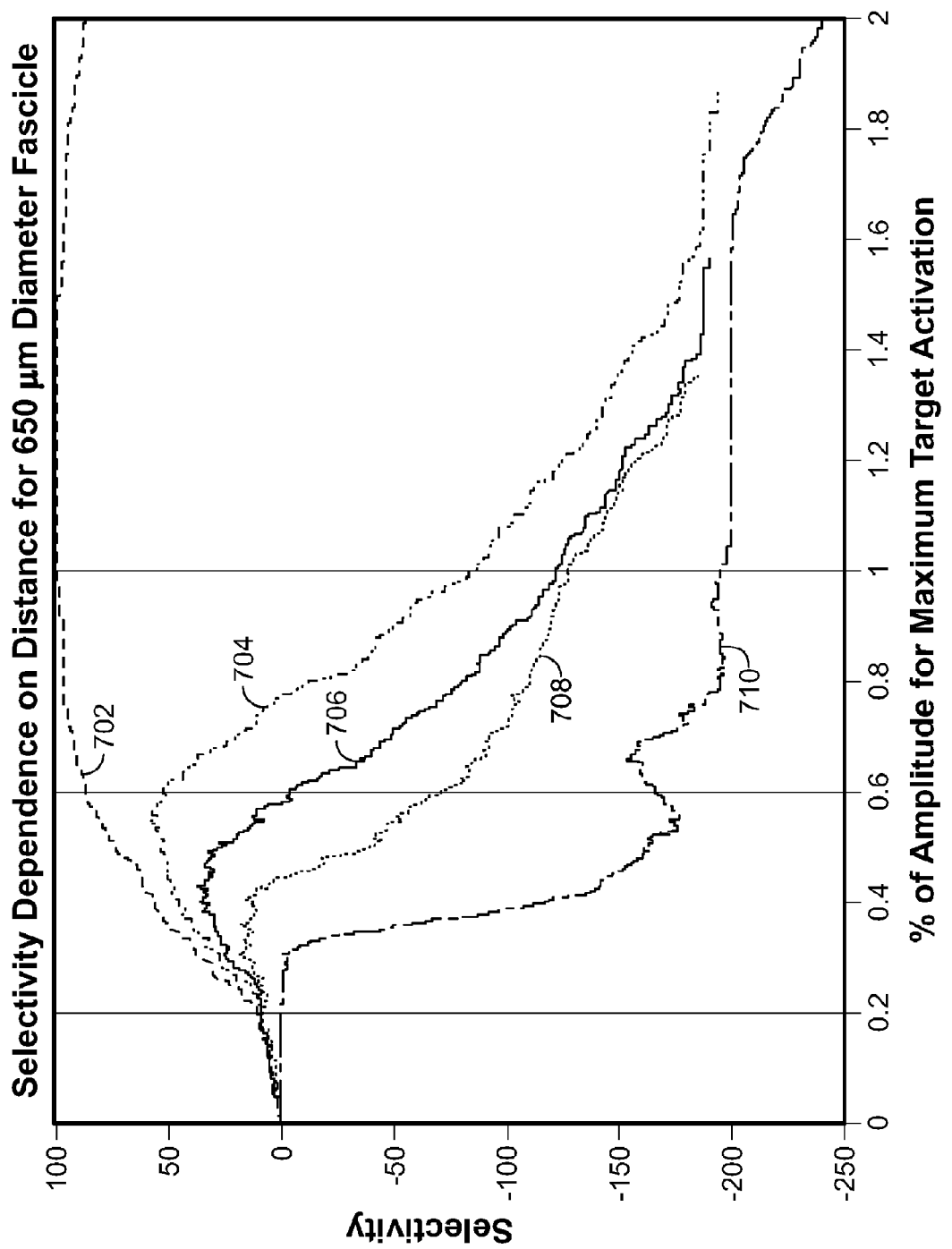
FIG. 7 illustrates a graph of a computer simulation for a single contact placed within the nerve at various distances from the target fascicle.
Figure 8:
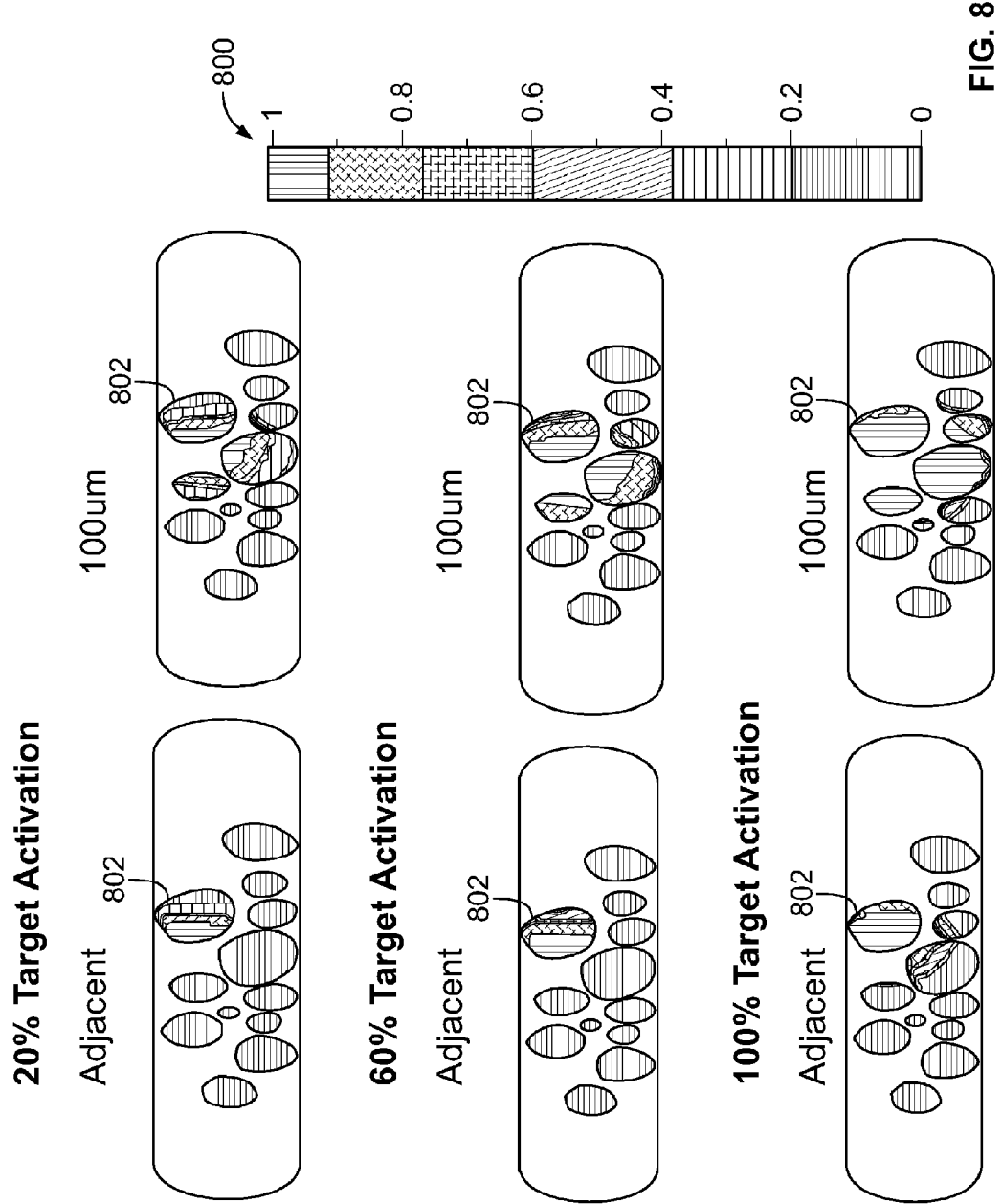
FIG. 8 illustrates cross sections of a simulated nerve under various contact placements and various activation levels.

FIGS. 7 and 8 show the results of a computer simulation demonstrating the selectivity of a single contact placed within the nerve and at various distances from the target fascicle. The plot shown in FIG. 7, illustrates the selectivity for contacts directly next to the fascicle shown as line 702, 10 um from the target fascicle shown as line 704, 50 um from the target fascicle shown as line 706, and 100 um from the target fascicle shown as line 708 as compared to a contact on the surface of the nerve shown as line 710. A selectivity value of 100 reflects perfect selectivity for the target fascicle and can be achieved if the contact is in direct contact with the fascicle. The selectivity drops, but is still desirable as the distance between the fascicle and contact is increased. FIG. 8 illustrates the areas of activation at the point indicated by the grayscale 800 for two contact-fascicle separations. The two columns correspond to contact placement adjacent to the target fascicle and 100 um from the target fascicle, which in all of the simulations in FIG. 8 is the upper right fascicle 802. The three rows correspond to higher 20%, 60% and 100% of target activation.

Figure 9:
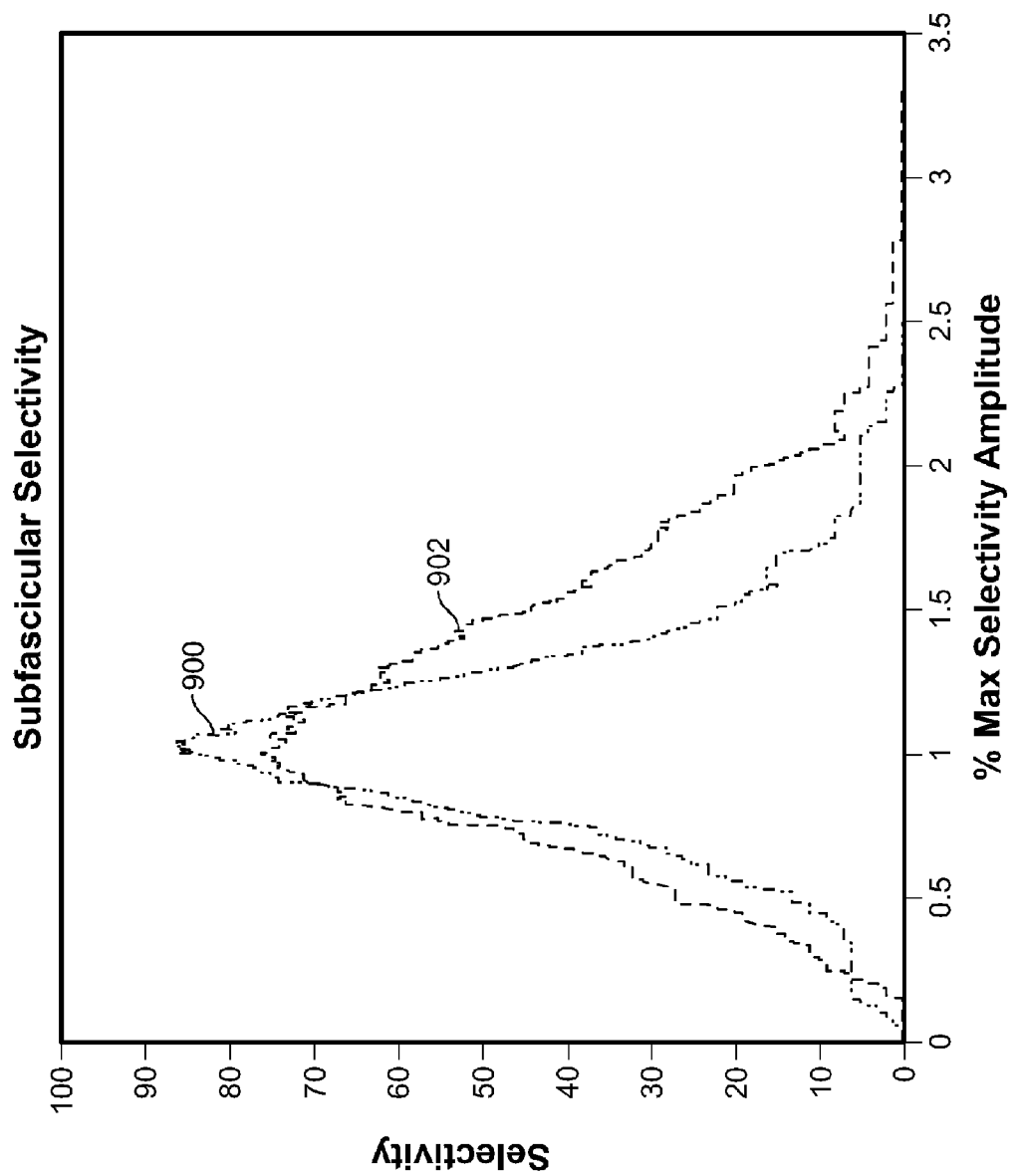
FIG. 9 illustrates a graph of subfascicular selectivity at certain percent levels of selectivity amplitude.
Figure 10:
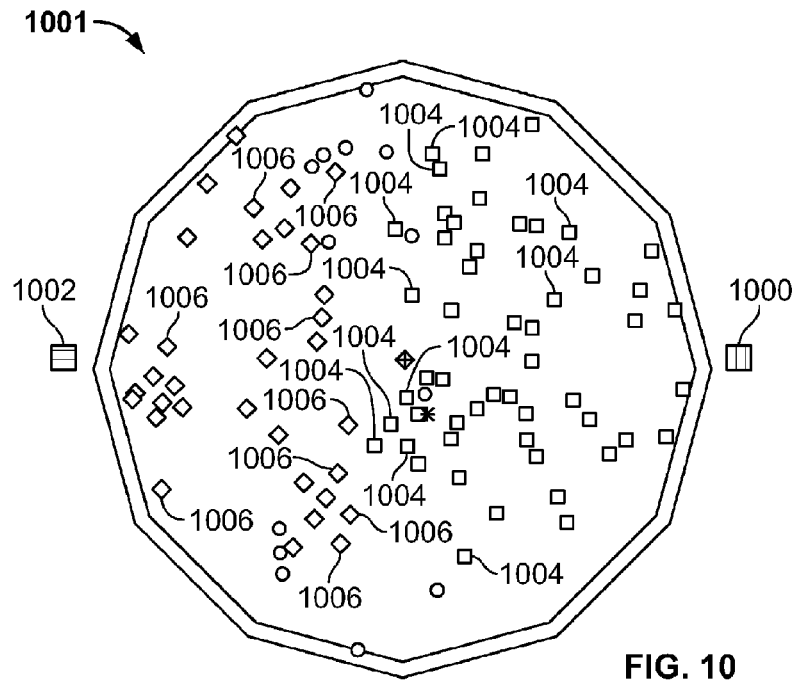
FIG. 10 illustrates locations of activations for contacts 1000, 1002.

FIGS. 9 and 10 illustrate results of a simulation for sub-fascicular selectivity. FIG. 9 shows a graph of subfascicular selectivity at certain percent levels of selectivity amplitude. The line 900 represents interfascicular placement while line 902 represents intrafascicular placement. FIGS. 9 and 10 show that each of the contacts 1000, 1002 outside the nerve 1001 excite about 80% of the fibers in the closest half of the fascicle without activation of any fibers on the other side. FIG. 10 illustrates the locations of activations, with activated fibers shown with an x, while non-activated fibers are shown with an oval shape. For example, fibers 1004 activated by contact 1000 are on the right side of the nerve 1001, while fibers 1006 activated by contact 1002 are isolated on the left side of the nerve 1001. The simulations also show that two electrodes outside of the fascicle are as selective as two contacts placed directly within the fascicle.

Figure 11:
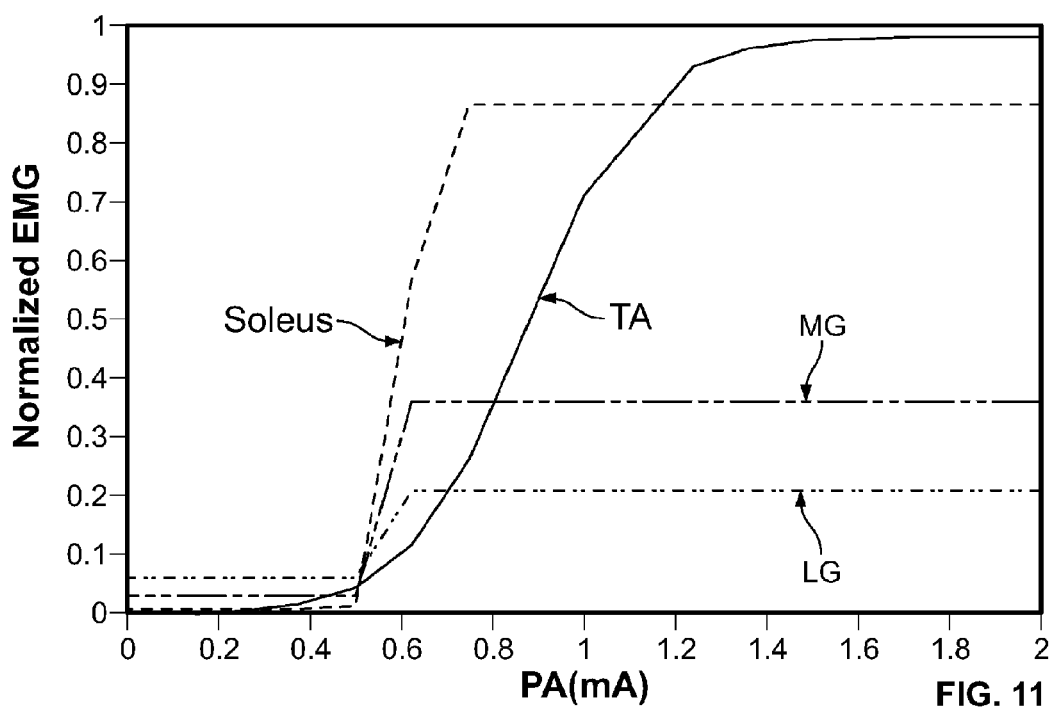
FIGS. 11-13 illustrate a graph of the results of stimulations having multiple contact points in single sciatic nerve of a rabbit.
Figure 12:
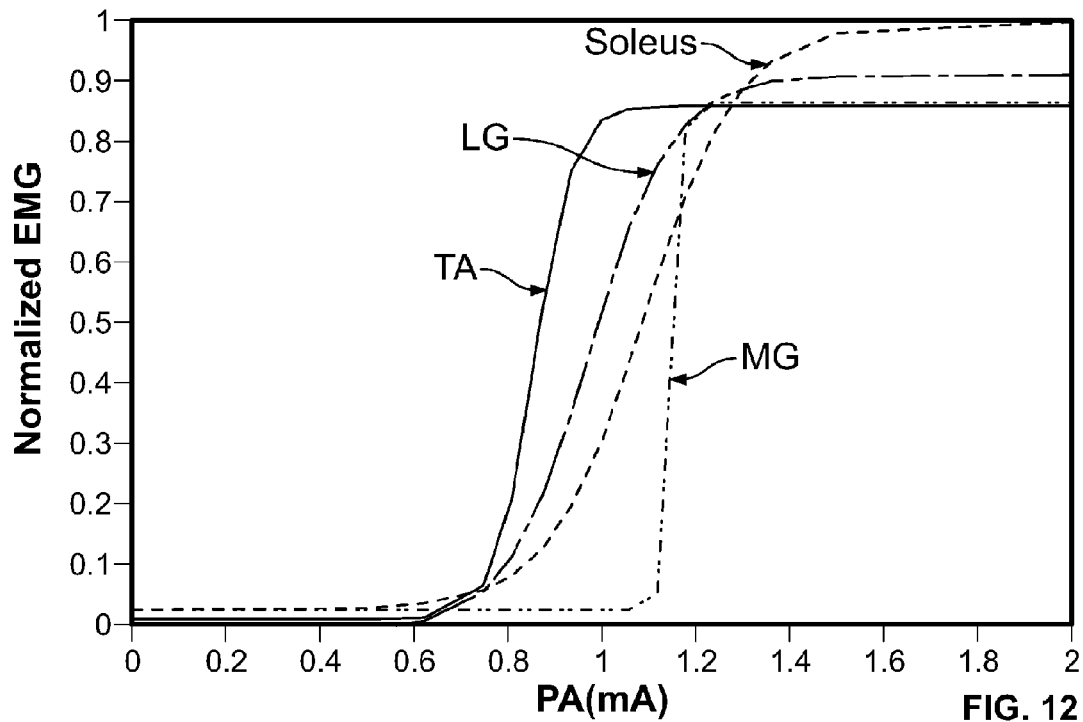
Figure 13:
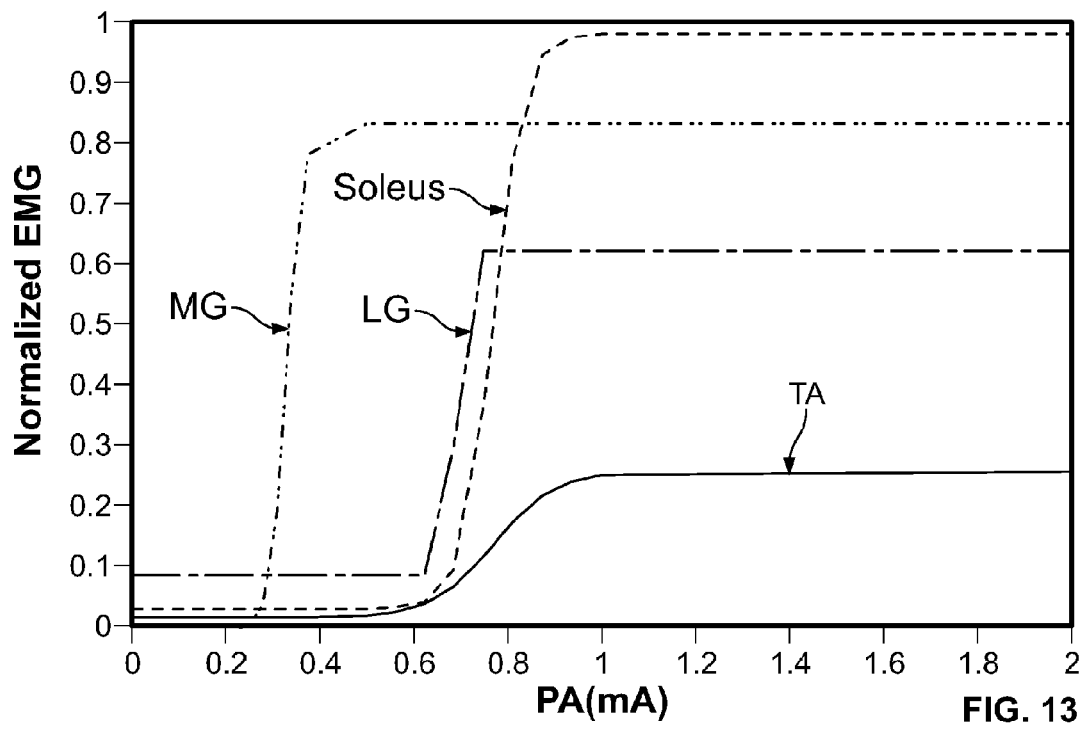

FIGS. 11 through 13 illustrate the results of a stimulation of multiple contact points in single sciatic nerve of a rabbit. The effected muscles are the Tibialis Anterior muscle, abbreviated "TA," the Lateral Gastrocnemius muscle, abbreviated "LG," the Medial Gastrocnemius muscle, abbreviated "MG" and the "Soleus" muscle. As shown in FIGS. 11 through 13, three completely different recruitments are possible. Thus, multiple point sources within the nerve may produce multiple different outputs.

For the purposes of this disclosure and unless otherwise specified, "a" or "an" means "one or more." To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or multiple components. As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term. From about X to Y is intended to mean from about X to about Y, where X and Y are the specified values.

While the present disclosure illustrates various embodiments, and while these embodiments have been described in some detail, it is not the intention of the applicant to restrict or in any way limit the scope of the claimed invention to such detail. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's claimed invention. Moreover, the foregoing embodiments are illustrative, and no single feature or element is essential to all possible combinations that may be claimed in this or a later application.

The invention claimed is:

1. A method comprising:
   extending a plurality of fibers from a housing, wherein each of the plurality of fibers comprises a conductive wire;
   covering each fiber with a layer of polymeric material to form a non-conductive sheath, wherein the polymeric material is rigid outside a nerve and flexible inside the nerve; and
   exposing a conducting region on each of the plurality of fibers, wherein the conducting region is exposed by an opening in the polymeric material.

2. The method of claim 1, wherein the conducting region on each fiber is located on one side of the respective fiber.

3. The method of claim 1, wherein the size of the conducting region on each fiber is small compared to the length of each fiber.

4. The method of claim 1, wherein the polymeric material comprises a variable tensile modulus and tensile strength.

5. The method of claim 1, further comprising coupling the plurality of conductive wires to a control unit with one or more leads.

6. The method of claim 5, wherein the control unit comprises at least one of monitoring circuitry, electrical signal generating circuitry and a user interface.

7. The method of claim 1, wherein the plurality of fibers is cylindrical in shape.

8. The method of claim 7, wherein the plurality of fibers comprises sharp tips.

9. The method of claim 1, wherein the polymeric material comprises a nanocomposite.

10. The method of claim 9, wherein the nanocomposite comprises ethylene oxide-epichlorohydrin combined with a cellulose matrix.

11. The method of claim 9, wherein the nanocomposite comprises at least one of an alkylene oxide, an epichlorohydrin, a vinyl aromatic copolymer, a polyolefin, a diene, a polyacrylate, a polyamide, and a polyester.

12. The method of claim 1, wherein the conducting region is configured for neural stimulation or neural recording.

13. A nerve interface electrode comprising a plurality of fibers, wherein each of the plurality of fibers comprises:
    a conductive core;
    a non-conductive sheath covering the conductive core, wherein the conductive sheath comprises a polymeric material that is rigid outside a nerve and flexible inside the nerve; and
    a conducting region where the conductive core is exposed by an opening in the polymeric material.

14. The nerve interface electrode of claim 13, wherein the conducting region is configured to be exposed to the interior of the nerve.

15. The nerve interface electrode of claim 13, wherein the polymeric material comprises a variable tensile modulus or tensile strength.

16. A system comprising:
    a plurality of fibers extending from a housing, wherein each of the plurality of fibers comprises:
    a conductive core;
    a non-conductive sheath covering the conductive core, wherein the conductive sheath comprises a polymeric material that is rigid outside a nerve and flexible inside the nerve; and
    a conducting region where the conductive core is exposed by an opening in the polymeric material; and
    a control unit coupled to the plurality of fibers comprising one or more leads.

17. The system of claim 16, wherein the conducting region on each fiber is located on one side of the respective fiber.

18. The system of claim 16, wherein the size of the conducting region on each fiber is small compared to the length of each fiber.

19. The system of claim 16, wherein the polymeric material comprises a variable tensile modulus and tensile strength.

20. The system of claim 16, wherein the control unit comprises at least one of monitoring circuitry, electrical signal generating circuitry and a user interface.

* * * * *